US010557830B2

(12) United States Patent
Colin

(10) Patent No.: US 10,557,830 B2
(45) Date of Patent: Feb. 11, 2020

(54) ACOUSTIC MEANS FOR DETECTING, LOCATING AND ASSESSING IMPACTS TO WHICH A STRUCTURE IS SUBJECTED

(71) Applicant: AIRBUS, Blagnac (FR)

(72) Inventor: Nicolas Colin, Nantes (FR)

(73) Assignee: AIRBUS, Blagnac (FR)

( * ) Notice: Subject to any disclaimer, the term of this patent is extended or adjusted under 35 U.S.C. 154(b) by 108 days.

(21) Appl. No.: 15/568,477

(22) PCT Filed: Apr. 21, 2016

(86) PCT No.: PCT/EP2016/058950
§ 371 (c)(1),
(2) Date: Oct. 21, 2017

(87) PCT Pub. No.: WO2016/170084
PCT Pub. Date: Oct. 27, 2016

(65) Prior Publication Data
US 2018/0143163 A1    May 24, 2018

(30) Foreign Application Priority Data
Apr. 21, 2015   (FR) ...................................... 15 53579

(51) Int. Cl.
*G01N 29/04*    (2006.01)
*G01N 29/14*    (2006.01)
(Continued)

(52) U.S. Cl.
CPC ............. *G01N 29/045* (2013.01); *B64F 5/60* (2017.01); *G01N 29/14* (2013.01);
(Continued)

(58) Field of Classification Search
CPC .. G01N 29/045; G01N 29/14; G01N 29/2481; G01N 29/46; G01N 2291/0231; G01N 2291/2694; B64F 5/60
(Continued)

(56) References Cited

U.S. PATENT DOCUMENTS 5,773,721 A  *  6/1998  Bashyam ............... G01B 17/06
                                              600/459
7,511,711 B2 *  3/2009  Ing ........................ G06F 3/0433
                                              345/173

(Continued)

FOREIGN PATENT DOCUMENTS

EP    2 538 241 A2    12/2012
FR    2 882 596 A1    9/2006
GB    2 492 456 A     1/2013

*Primary Examiner* — Natalie Huls
*Assistant Examiner* — Monica S Young
(74) *Attorney, Agent, or Firm* — Im IP Law; Chai Im; C. Andrew Im

(57) ABSTRACT

A device which detects and locates an impact on a structure. The device includes at least three acoustic sensors so that an acoustic wave emitted at any point of a measurement space can be received through direct propagation by each of the sensors. The device also includes command controller configured to process the signals corresponding to the acoustic waves received by the acoustic sensors, to detect the occurrence of an impact, and to locate a point of the structure that is the source of an acoustic wave. At least one optical pointer is actuated by the command controller so as to designate an impact point located on the structure by illuminating a corresponding site of the structure.

12 Claims, 2 Drawing Sheets

(51) Int. Cl.
*G01N 29/24* (2006.01)
*G01N 29/46* (2006.01)
*B64F 5/60* (2017.01)

(52) U.S. Cl.
CPC ......... *G01N 29/2481* (2013.01); *G01N 29/46* (2013.01); *G01N 2291/0231* (2013.01); *G01N 2291/2694* (2013.01)

(58) Field of Classification Search
USPC .......................................................... 73/633
See application file for complete search history.

(56) References Cited

U.S. PATENT DOCUMENTS

| | | | | |
|---|---|---|---|---|
| 8,930,042 | B2* | 1/2015 | Jang | G01N 29/225 701/2 |
| 8,982,207 | B2* | 3/2015 | Jang | B64F 5/60 348/128 |
| 9,352,851 | B2* | 5/2016 | Tudor | B64F 5/60 |
| 9,952,593 | B2* | 4/2018 | Colin | B25J 5/007 |
| 10,371,646 | B2* | 8/2019 | Boyer | B25J 9/046 |
| 2003/0089183 | A1* | 5/2003 | Jacobsen | G01N 29/045 73/865.8 |
| 2003/0217873 | A1* | 11/2003 | Paradiso | G06F 3/0433 178/18.04 |
| 2004/0134280 | A1* | 7/2004 | Hedberg | G01N 3/30 73/579 |
| 2005/0212777 | A1* | 9/2005 | Ing | G06F 3/0433 345/173 |
| 2010/0198528 | A1* | 8/2010 | McCauley | A63B 24/0021 702/41 |
| 2010/0235037 | A1* | 9/2010 | Vian | G07C 5/008 701/31.4 |
| 2011/0112775 | A1* | 5/2011 | Bramban | G01B 17/04 702/56 |
| 2013/0160553 | A1* | 6/2013 | Gruca, Jr. | G01N 29/048 73/632 |
| 2013/0261876 | A1* | 10/2013 | Froom | G01M 5/0016 701/29.3 |
| 2014/0165728 | A1 | 6/2014 | Chaume et al. | |
| 2015/0040650 | A1* | 2/2015 | Lacaille | G01M 15/14 73/112.01 |
| 2017/0139031 | A1* | 5/2017 | Salloum | G01S 3/802 |

* cited by examiner

ACOUSTIC MEANS FOR DETECTING, LOCATING AND ASSESSING IMPACTS TO WHICH A STRUCTURE IS SUBJECTED

RELATED APPLICATIONS

This application is a § 371 application from PCT/EP2016/058950 filed Apr. 21, 2016, which claims priority from French Patent Application No. 15 53579 filed Apr. 21, 2015, each of which is incorporated herein by reference in its entirety.

FIELD OF THE INVENTION

The invention relates to the general problem of quality control in the fields of the manufacture and repair of parts and structures. The invention relates more particularly to the detection of impacts that might have been undergone by parts for which a rigorous quality monitoring must be assured, such as, for example, the aeronautical parts and structures made of composite material that can suffer damage during the manufacture, the assembly or the repair thereof.

BACKGROUND OF THE INVENTION

Structural damage occurs not only during the commercial or operational operation of an aircraft. Such damage can also be caused by operatives working at the stage of the construction or final assembly of the aeronautical parts.

Thus, when an operator drops, for example, a tool on a structure, or when a driver of a motorized vehicle, moving within an assembly area, accidentally strikes a fuselage being assembled, it may be that, for various reasons, this incident is not detected such that any damage, undetectable by simple visual inspection, particularly in the case of structures made of composite materials, cannot be identified or repaired before the delivery of a subassembly, before final assembly of the structures or before delivery to the client.

It follows that, to achieve the level of reliability and quality demanded of the structures delivered, checks must be performed and that, in the case where damage is observed very late in the assembly phase, its repair results in a loss of time that can create delivery delays which are generally reflected by financial penalties borne by the aircraft manufacturer.

There are currently no technical means that make it possible, simply and automatically, in other words without the intervention of an operator, to detect and identify incidents of this type occurring within a manufacturing or assembly area and for transmitting to a control authority alert information likely to bring about the implementation of a procedure intended to assess the damage and rapidly decide on the need to proceed with a repair.

Consequently, the only measures currently implemented, apart from a systematic final inspection of all of the assembly requiring inspection means capable of detecting damage that cannot be detected by visual inspection, consists in strict procedures with the aim of making each operator responsible such that the flagging of any incident of this type, when it is noticed, is not omitted. Such procedures can, in extreme cases, include a constant visual surveillance of the manufacturing or assembly area concerned by operators assigned to this task.

SUMMARY OF THE INVENTION

One aim of the invention is to propose a device that can operate continuously and without interfering with the people working in the environment of a structure to detect, in real time, abnormal events of the "impacts on the structure" type.

It is thus possible to intervene in the best conditions in the case of the occurrence of these abnormal events, in particular to intervene as early as possible at a stage where the inspections and any repairs will be least expensive.

To this end, the subject of the invention is a device for performing the detection and the location of an impact on a structure, situated in a measurement volume and in which operators and/or vehicles move around.

The device comprises:
  at least three acoustic sensors arranged non-aligned inside the measurement volume and such that an acoustic wave emitted at any point of the measurement volume can be received by direct propagation by each of the sensors;
  command and control means configured to process the signals corresponding to the acoustic waves received by the at least three acoustic sensors in order to detect an occurrence of an impact on the structure and in order to locate a point of said structure that is the source of an acoustic wave following the impact and detected by the acoustic sensors.

Thus, with no intervention from the people working on the structure, and with no hindrance caused to these people in their activities, impacts occurring on the structure, and the location of the impacts on the structure, are detected.

Through a suitable sensitivity of the acoustic sensors, advantageously microphones, impacts that are inaudible or whose intensity would not be perceived by the people working on the structure, can be detected and avoid late interventions following a fault discovered subsequently.

In one embodiment, the device also comprises at least one optical pointer remotely producing a spot illumination, for example in the form of a visible light spot, and positioned in the measurement volume such that points of a structure in the measurement volume can be illuminated by the at least one optical pointer, said optical pointer being actuated by the command and control means so as to designate an impact point located on the structure by illuminating a corresponding location of the structure.

Thus, the location of an assumed impact on the structure is directly and visibly identified without interpretation by an operator.

In one embodiment, the command and control means are configured so as to identify and designate the source of an acoustic emission only if the latter is situated in a limited zone of the measurement volume encompassing the volume actually occupied by the structure.

Thus, the zones not affected by the surveillance performed by the device do not produce alerts which would a priori not be of interest such as impacts produced by a normal activity in the context of a workshop and the handling of tools.

In one embodiment, an analysis of the sound waves received by the sensors comprises a continuous determination of the respective amplitudes and frequencies of the acoustic waves received and a determination of an ambient noise level and spectrum, integrated over a determined time, a deviation between an acoustic signal level measured at a given instant and an acoustic signal level from the ambient noise being compared to a fixed threshold.

The acoustic signals that can result from an exceptional event are thus discriminated, as in the case of an impact on the structure.

In one embodiment, the command and control means are also configured so as to characterize the impact detected, from an amplitude and a spectrum of the acoustic wave received.

Information is thus provided for the attention of the operators concerning the nature and the intensity of the causes that might have lead to the acoustic wave observed, for example by referring to a catalog of known events.

Advantageously, the command and control means are also configured to eliminate spurious acoustic waves such as the multiple reflections of the acoustic waves on walls and on objects, other than the structure, contained in the measurement volume.

The number of fault detections which could trigger pointless investigations is thus limited.

The command and control means perform the location of the impact point by triangulation, and/or by trilateration, and/or by analysis of the amplitude and/or phase differences between the signals corresponding to the acoustic waves received by the acoustic sensors.

Through the implementation of these methods taken independently, or in combination to improve the accuracy thereof if necessary, a location on the structure of the source of the acoustic wave is obtained.

The accuracy of this location can be less than, at least in theory, a centimeter subject to the quality of the measurement chain implemented.

The command and control means perform the visual designation of a located impact point by directing the light beam emitted by the at least one optical pointer so as to illuminate a location in the volume of the monitored space from which a received acoustic wave is assumed to originate and correspond to an impact point.

Preferably, the device comprises a plurality of optical pointers arranged in the measurement volume, a priori arranged in said measurement volume or in proximity thereto, to make it possible to illuminate points of different zones of the structure on which zones impacts must be detected in the case of occurrence of an impact.

It is advantageous to distribute these pointers in the measurement volume or in proximity to this volume to ensure the possibility of pointing at, if not all, at least the maximum of zones of the structure likely to have an impact. The multiplicity of the pointers limits the shadow zones, for example created by the structure itself or by tools, likely to prevent particular points of the monitored structure from being illuminated.

In one embodiment, the acoustic sensors are directional sensors positioned around the zone of the enclosure in which the structure is located and oriented toward the latter so as to cover all or part of the volume of said structure.

The limits of the monitored zone are thus improved and the processing of the signals of no interest with respect to the detection of the impacts is avoided.

To take account of the real conditions in the measurement volume, advantageously, the positions of the acoustic sensors and of the optical pointers are recorded, the recorded positions then being stored by the command and control means.

Advantageously, the optical pointers are laser pointers producing a quasi-spot illumination in the visible domain, of which the light spot formed on the structure is of small dimensions even with relatively distant pointers and remains visible in the ordinary lighting conditions of a workshop.

The invention therefore consists essentially of an acoustic means sensitive in the audible domain and associated electronics intended to detect, identify, locate and quantify automatically the impacts on the structures, such as aeronautical structures, which can take place in a production plant or on a final assembly line of the major manufacturers. An optical means for designating located zones on the structures is preferably associated with the acoustic means.

DESCRIPTION OF THE FIGURES

The features and advantages of the invention will be better appreciated from the following description, which description is based by way of exemplary embodiment on the attached figures which present.

The elements present on the two figures are referenced by the same reference number.

DETAILED DESCRIPTION

Generally, the invention consists firstly in implementing, in an enclosure 12, a production or assembly hangar for example, delimiting in this example a measurement volume 12a where a structure 11 concerned is placed, several "electronic ears" sensitive to sounds, so as to pick up the acoustic waves produced by said structure in response to impacts received, impacts provoked for example by the dropping of tools or the collision of vehicles 16 moving around in the enclosure in the vicinity of the structure 11.

The structure 11 considered is for example, as in the example illustrated by the figures, an aeronautical structure (aircraft fuselage or wing in particular) produced wholly or partly in composite material or even in metal. However, the device is of course applicable to other types of structures.

Figure 1:
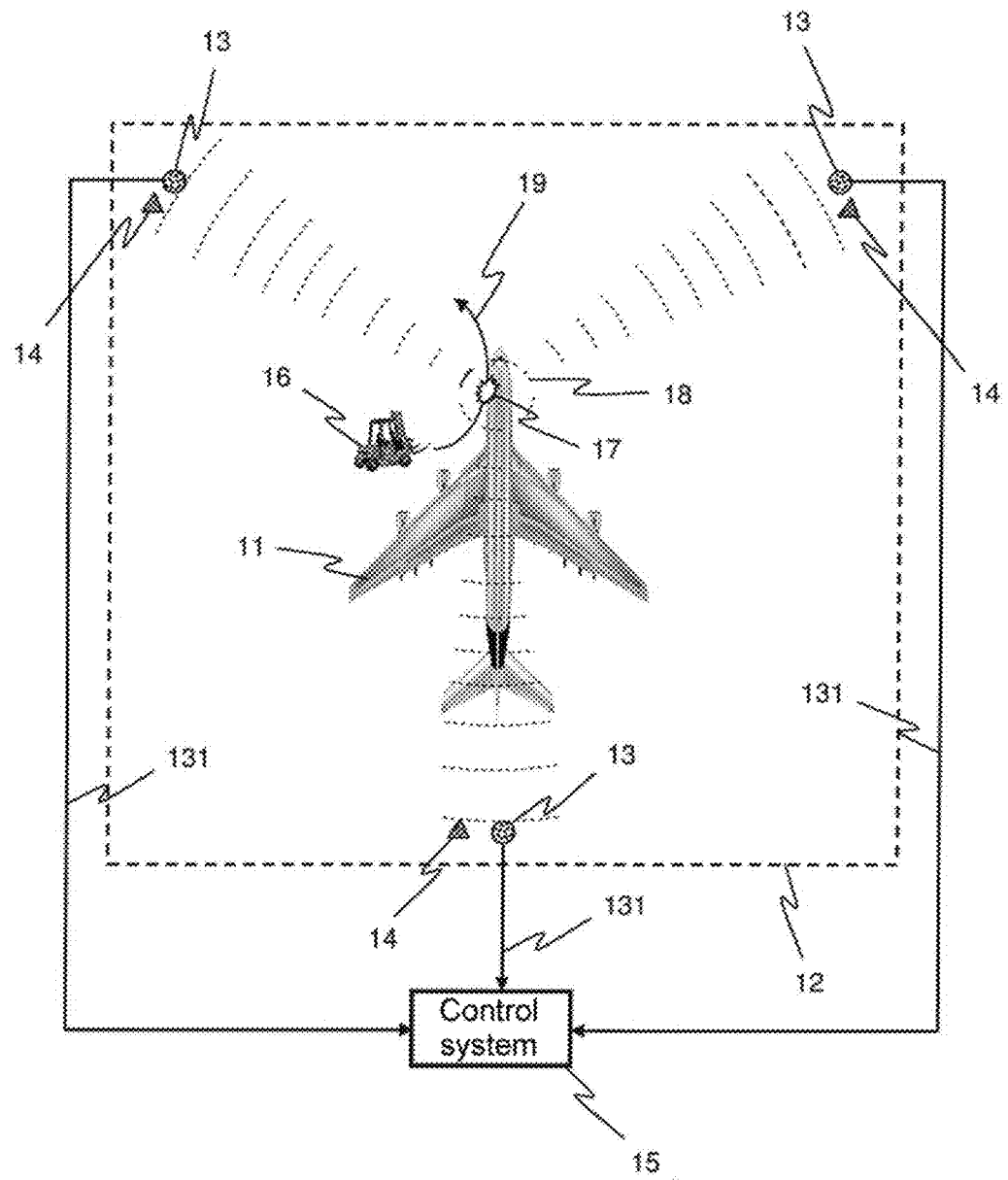
FIG. 1, a first schematic illustration presenting the device according to the invention.

As illustrated by FIG. 1, the device according to the invention comprises a plurality of acoustic sensors 13 positioned in the measurement volume 12a, or immediately nearby, arranged so as to receive an acoustic wave 18 emitted by the structure 11 in response to an impact.

The acoustic sensors 13 are consequently chosen with a sensitivity and a range of frequencies suited to the sounds emitted and which must be detected in the context of the surveillance that has to be ensured in the measurement volume.

Such parameters are in practice a function of the dimensions of the measurement volume, which partly conditions a distance between the acoustic sensors and the locations of a structure that may be the source of an acoustic wave, and possibly other characteristics of the acoustic sensors such as their directivity.

Said sensors, at least three sensors, are positioned in the measurement volume so as not to be located all aligned.

Generally, the sensors 13 can be positioned, in sufficient numbers, so as to detect an acoustic wave with at least three sensors in, as far as possible, all of the interior space of the enclosure. However, in a particular implementation of the invention, the number of sensors 13 used and their positions in the enclosure 12 can be defined so as to cover a more restricted measurement volume 12a within the enclosure, for example a volume encompassing the structure 11 and its more or less immediate vicinity.

According to the invention, the acoustic sensors 13 used are preferentially microphones exhibiting a directivity pattern, prioritizing the detection of the acoustic waves in the direction of the structure so as to cover at least all of the zone of the measurement volume in which the structure 11 is situated, or limited for a determined part of the structure, said directivity pattern being chosen to limit the sensitivity of the microphone concerned to the waves originating from directions other than those of the structure or part of monitored structure, to the waves reflected by the walls of the enclosure 12 in particular.

However, omnidirectional microphones can also be used, other methods, of processing of the signal in particular or even treatment of walls of the enclosure 12 to limit the acoustic reflections, being able to be implemented so as not to take account of the acoustic waves unrelated directly with the structure.

According to the invention also, the acoustic sensors 13 are linked to a command and control system 15 to which acoustic measurements are transmitted from each of the sensors, for example in the form of electrical signals produced by the conversion of the acoustic waves 18 received by each of the sensors 13. The links between the command and control system 15 and the acoustic sensors 13, represented by the links 131 in FIG. 1, can be simple wired links or alternatively, in the case where the sensors used are emitting microphones, radiofrequency links of various types (links with dedicated frequencies, Bluetooth® links, etc.).

According to different system architectures, the acoustic measurements performed by a sensor are transmitted to the command and control system 15 in analog form or transmitted in digital form after having been converted by the sensor or electronics associated with the sensor.

Whatever the transmission mode implemented between the sensors 13 and the command and control system 15, the necessary precautions will be taken to ensure that the acoustic signals, having the same origin on the structure 11, received by different sensors 13 and transmitted to the command and control system 15, are dated so that the moment when an acoustic signal reaches a sensor is identified accurately, at least relatively between the different sensors.

The dating can be performed by the sensor itself provided that each sensor receives a clock signal or has a clock synchronized on a time base common to all the sensors.

The dating can be performed by the command and control system when it receives the signals from the different sensors, provided that the signal transmission chains between each sensor and the command and control system do not introduce significant time differences between the different sensors, or at the very least that these signal transmission time differences are known and controlled.

In the present device, it is essential to take account of the fact that the synchronization of the measurements performed by the different sensors, the accuracy of which conditions the result sought, addresses acoustic signals whose propagation speeds in ordinary atmospheric conditions are of the order of 300 m/s.

It is deduced therefrom that a synchronization with an accuracy of 0.1 millisecond introduces measurement errors of the order of a centimeter over distances, which corresponds to a sufficient accuracy for the needs of the location of an event on the structure 11.

Ordinary electronic means make it possible, without difficulty, for a person skilled in the art to guarantee a signal dating accuracy of 0.1 millisecond or less.

The command and control system 15, for its part, primarily comprises means for acquiring and storing electrical signals transmitted by the acoustic sensors, the acquisition being performed continuously; these signals being possibly multiplexed on a single acquisition channel.

The command and control system 15 also comprises means for performing the processing of these signals, advantageously in digital form, so as to identify the signals corresponding to an acoustic wave 18 resulting from an impact 17 on the structure 11, and a computer (of PC type for example) equipped with software for interpreting the signals detected, and for characterizing the corresponding impact (nature, position, intensity, etc.).

To do this, the digital processing means according to the invention perform the measurement of the amplitude of each of the signals received and proceed with a time and frequency analysis.

They also continuously perform an estimation of the amplitude and of the spectrum of the noise environment (i.e. of the ambient noise) and record the noise environment repetitively over given times, a time of a minute for example, so as in particular to determine the frequencies and an amplitude threshold that make it possible to distinguish the signals of interest out of the signals a priori constituting the ambient noise.

Moreover, the digital processing means also perform the elimination by any appropriate known method, spectral analysis or correlation in particular, of the signals corresponding to the spurious sound waves received by the acoustic sensors 13, the waves originating from multiple reflections in particular.

According to the invention, the detection and the characterization of the signals of interest can be performed in different ways.

The detection can thus be performed by comparing the measured amplitude to one or more amplitude thresholds characterizing the amplitude of the acoustic wave emitted by the structure as well as by spectral analysis, these parameters supplying general qualitative information on the nature of the impact, simple dropping of tools or collision with a vehicle 16 moving around 19 in proximity to the structure.

Alternatively, in the case where the command and control system includes a database in which acoustic energy thresholds are stored coupled with certain frequency spectra previously determined and corresponding to known impacts between tools or other objects and structures of the same type as the structure 11 concerned, the identification of a signal of interest with one or other of the impacts already listed makes it possible to have more accurate information on the amplitude, the origin and the nature of the potential damage caused.

The digital processing means also perform, when signals of interest have been detected, a location of a zone 17 of the structure as being the probable source of the acoustic wave 18 corresponding to these signals, in practice the zone of the structure having undergone an impact, and potentially damage.

This location is performed by any known method from the acoustic signals picked up by the different sensors 13 positioned in the measurement volume 12a, for example by triangulation (goniometric analysis), and/or by trilateration (analysis of the signal reception date differences), and/or analysis of the amplitude and/or phase differences between the acoustic signals received by the different sensors.

For example, the measurement of a time difference between the instants when an acoustic signal is received by each of two sensors, the signals being identified as having the same source for example because of the similarities of their spectra, makes it possible to calculate a surface, a hyperboloid, of the space which corresponds to the set of the points of the space for which the difference in the distances to the two points defined by the position of the sensors is constant, said difference in the distances being in this case the distance traveled by an acoustic signal, in the physical conditions of the enclosure, during the difference in measured times of reception of the acoustic signals. As is known, the sensors, whose positions in the measurement space are known, then correspond to the positions of the focuses of the hyperboloid.

The surfaces are then calculated for each set of two sensors, i.e. three surfaces corresponding to the cases of three sensors considered two by two, and the intersections of these surfaces lead to the determination of a point, or of a volume depending on the measurement uncertainties, which at least in theory is the source of the acoustic wave received by each sensor. This result is obtained provided that the three sensors considered are not aligned and that the source of the acoustic wave emitted is not located in the plane determined by the three sensors, which can in general be obtained by an arrangement of the three sensors such that the plane that they determine is not secant with the monitored structure.

It should be noted that while, in practice, the method leads to mathematically identifying several points as being a possible source of the acoustic wave emitted, only the points situated in a volume actually occupied by the monitored structure will be considered, the points situated outside of this volume being able to be eliminated.

It should also be noted that while at least three sensors must be implemented to determine a location, an increase in the number of sensors 13 in the measurement volume 12a, in addition to it making it possible to limit the number or the dimensions of the masked zones of the structure 11, makes it possible to eliminate any ambiguities and improve the accuracy with which the zone of an impact on the structure can be located.

As already specified, the determination of a time difference, equivalent to a distance, with which the acoustic signals from one and the same origin are received by two sensors, presupposes that the signals are dated with the required accuracy.

Once located, the position of the impact zone 17 is stored, possibly with the parameters describing the nature of the event, as it has been interpreted, that is the source of the impact (collision, dropped object, etc.).

According to the invention, the command and control system also comprises means making it possible to alert operatives responsible for managing such incidents, that an impact occurrence has been identified on the structure 11 and the point 17 at which the impact probably occurred. These means make it possible to undertake various actions according to the desired procedure. Said means can for example communicate the occurrence of an incident to an operator situated in a control room and responsible for managing incidents that can occur in the enclosure concerned.

The communication can then take the form of a message sent directly by the command and control system to the console of the operator, the message mainly comprising a position of the incident (coordinate of the impact point on the structure) and possibly a message indicating the probable cause of the damage.

Figure 2:
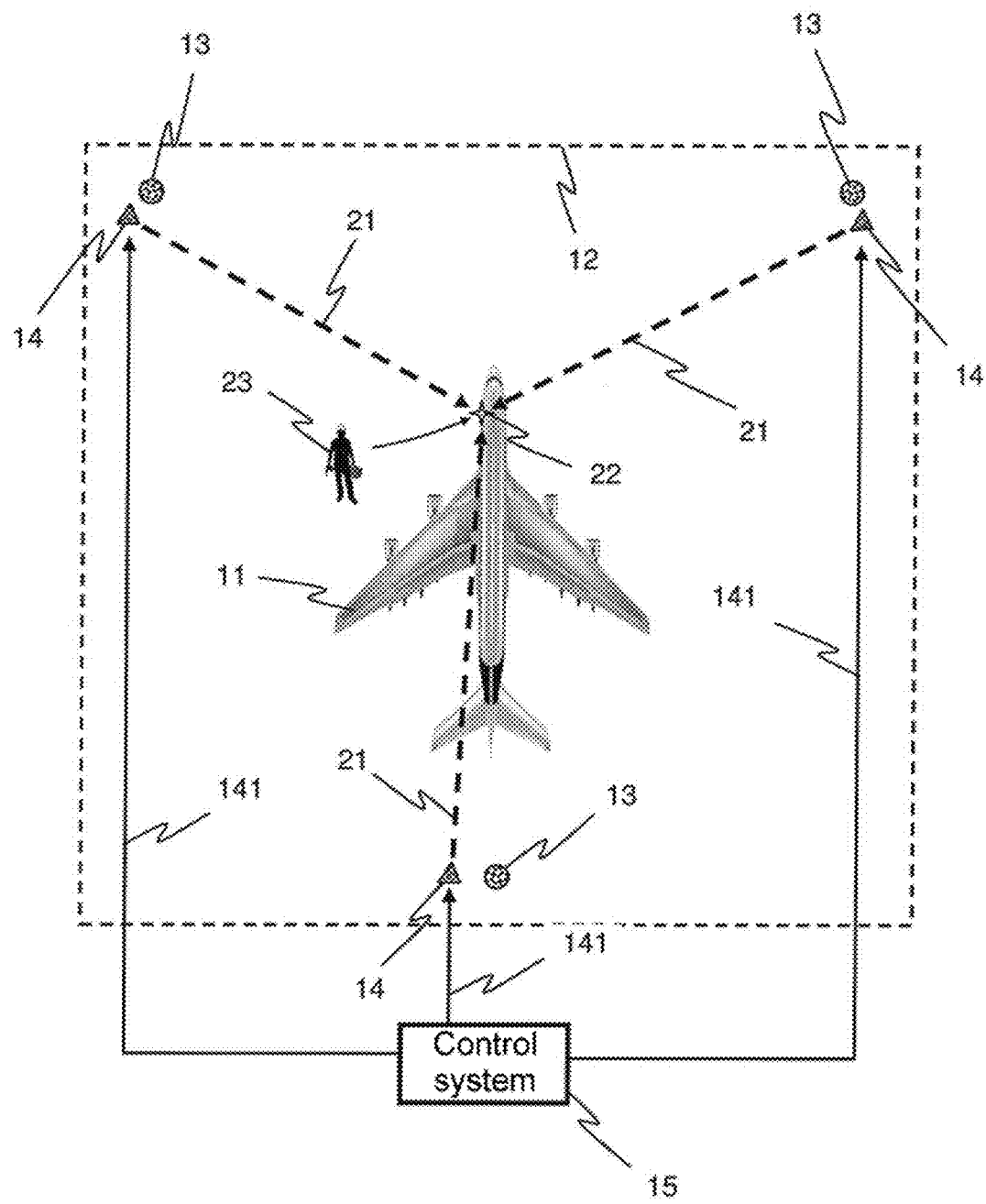
FIG. 2, a second schematic illustration presenting the device according to the invention.

The communication can also be complemented, in a preferred embodiment illustrated by FIG. 2, by the emission of a light beam 21 pointed to the located zone of the impact 17 and intended to visually flag this zone, by a light spot 22, to an operator 23 responsible for assessing the damage caused and for deciding a repair procedure.

In this embodiment, the device according to the invention then comprises a set of optical pointers 14 associated with the measurement volume 12a, for example positioned inside the enclosure 12, at known positions, so as to be able to direct at least one light beam on any point of the structure 11. According to the invention, the pointers 14 can be steered and driven by the command and control system 15 to which they are linked by links 141, wired or radiofrequency links, for receiving steering signals.

In a preferred embodiment, the optical pointers are laser sources emitting a light beam producing a substantially spot illumination on the structure.

Thus, if an incident has been detected, the device according to the invention assesses the energy of the impact caused as a function of the origin and of the amplitude of the sound wave then alerts a surveillance operator and indicates, possibly visually, the location on the structure that is the source of the acoustic wave that has been detected.

In a particular embodiment, the command and control means 15 are configured so as to identify and designate the source 17 of an acoustic emission only if the latter is identified as being situated in a limited zone of the measurement volume 12a encompassing the volume actually occupied by the structure 11.

Advantageously in this case, the command and control means 15 proceed with the optical designation only on instructions from an operator, for example emitted by the operator when he or she is on station in the measurement zone.

It should be noted that since a device such as that according to the invention is intended for autonomous operation, its placement in a given enclosure 12 includes, as necessary, a calibration phase, during which the device performs the acquisition of the respective positions of the different acoustic sensors and of the positions and orientations of the different optical pointers, as well as the acquisition of response curves of each of the sensors in the measurement conditions, for example by the implementation of calibrated sound sources.

The invention claimed is:

1. A non-contact device to detect and locate an impact on a structure, comprising:
   at least three non-contact acoustic sensors arranged non-aligned and positioned within a measurement enclosure in which the structure is located and in which at least one of operators and vehicles move around within and such that an acoustic wave emitted at any point of the measurement enclosure can be received by direct propagation by each of the non-contact acoustic sensors;
   a command controller configured to process signals corresponding to the acoustic waves received by said at least three non-contact acoustic sensors to detect an occurrence of an impact on the structure and to locate a point of the structure that is a source of an acoustic wave following the impact and detection by said at three non-contact acoustic sensors; and
   at least one optical pointer to produce a spot illumination at a distance from said at least one optical pointer, said at least one optical pointer positioned in the measurement enclosure such that points of the structure in the measurement enclosure can be illuminated by said at least one optical pointer, said at least one optical pointer being actuated by the command controller so as to designate a location in the measurement enclosure, from which a received acoustic wave is determined to originate, and correspond to an impact point located on the structure by illuminating a corresponding location of the structure.

2. The device as claimed in claim 1, wherein the command controller is configured to identify and designate the source of the acoustic wave only if the source is situated in a limited zone of the measurement enclosure encompassing a volume actually occupied by the structure.

3. The device as claimed in claim 1, wherein the processing of the signals corresponding to the acoustic waves received by said at least three sensors comprises a continuous determination of respective amplitudes and frequencies of the acoustic waves received, a determination of an ambient noise level and spectrum, integrated over a predetermined time, and comparing a deviation between a noise level measured at a given instant and the ambient noise level to a fixed threshold.

4. The device as claimed in claim 3, wherein the command controller is configured to eliminate spurious acoustic waves other than reflections of the structure contained in the measurement enclosure.

5. The device as claimed in claim 4, wherein the spurious acoustic waves are multiple reflections of the acoustic waves on walls on objects contained in the measurement enclosure.

6. The device as claimed in claim 1, wherein the command controller is configured to characterize the impact detected, from an amplitude and a spectrum of the acoustic wave received.

7. The device as claimed in claim 1, wherein the command controller determines the location of the impact point by applying at least one of the followings methods to the acoustic waves received by said at least three acoustic sensors: triangulation, trilateration, and analysis of the amplitude or phase differences.

8. The device as claimed claim 1, wherein the command controller visually designates a located impact point by directing a light beam emitted by said at least one optical pointer to illuminate a zone of the structure identified as the impact point.

9. The device as claimed in claim 1, comprising a plurality of optical pointers arranged in the measurement enclosure or in proximity to the measurement enclosure to illuminate points of different zones of the structure on which zones impacts must be detected in the event of occurrence of an impact.

10. The device as claimed in claim 1, wherein said at least three non-contact acoustic sensors are directional sensors and the directional sensors are oriented toward the structure.

11. The device as claimed in claim 1, wherein the command controller records and stores positions of said at least three acoustic sensors and of said at least one optical pointer.

12. The device as claimed in claim 1, wherein said at least one optical pointer is a laser pointer producing a quasi-spot illumination.

\* \* \* \* \*